United States Patent [19]
West et al.

[11] Patent Number: 4,779,629
[45] Date of Patent: Oct. 25, 1988

[54] MAKING MEASUREMENTS ON A BODY

[75] Inventors: Gordon M. West; Peter R. M. Jones, both of Loughborough, England

[73] Assignee: Loughborough Consultants Limited, Loughborough, England

[21] Appl. No.: 915,245

[22] Filed: Oct. 3, 1986

[30] Foreign Application Priority Data

Oct. 4, 1985 [GB] United Kingdom ............ 8524473

[51] Int. Cl.[4] .................................. A61B 5/10
[52] U.S. Cl. ...................... 128/774; 33/512; 33/515
[58] Field of Search .............. 128/774, 782; 33/511-512, 515; 364/556; 356/385-387, 376

[56] References Cited

U.S. PATENT DOCUMENTS

| 4,146,926 | 3/1979 | Clerget et al. | 364/556 |
| 4,473,750 | 9/1984 | Oshida et al. | 250/560 |
| 4,670,781 | 6/1987 | Aubert et al. | 128/774 X |

FOREIGN PATENT DOCUMENTS

| 0062941 | 3/1982 | European Pat. Off. | |
| 0168559 | 1/1986 | European Pat. Off. | 128/328 |
| 3508730 | 9/1986 | Fed. Rep. of Germany | 128/774 |
| 1078108 | 8/1967 | United Kingdom | |
| 2069690 | 1/1981 | United Kingdom | |
| 2030286 | 6/1983 | United Kingdom | |

OTHER PUBLICATIONS

A. Ishida et al., "Scoliosis Evaluation Utilizing Truncal Cross-Sections", Med. & Eng. & Computing, 20:181-186, (1982).
B. J. Thompson, "Computers in Radiation Therapy", 3rd Int. Conf. on Med. Phys., Götenborg, Sweden, (1972).

Primary Examiner—Max Hindenburg
Assistant Examiner—Angela D. Sykes
Attorney, Agent, or Firm—Merchant, Gould, Smith, Edell, Welter & Schmidt

[57] ABSTRACT

A method of making measurements on a body includes the steps of placing a body in a space which is divided along a plane into adjacent regions of contrasting illumination with the dividing plane intersecting the body, rotating the body relative to the dividing plane about an axis and sensing the position on the dividing plane of at least a part of the exterior surface of the body with a sensor sensitive to the illumination at a plurality of rotational positions of the body. The axis about which the body is rotated lies in the dividing plane and light sources which divide the space into adjacent regions of contrasting illumination are located on the dividing plane.

10 Claims, 2 Drawing Sheets

MAKING MEASUREMENTS ON A BODY

FIELD OF THE INVENTION

This invention relates to a method and apparatus for making measurements on a body. In particular the invention is concerned with making measurements on a human body although it encompasses making of measurements on other animate or inanimate bodies.

BACKGROUND OF THE INVENTION

Various techniques have been used in the past for making measurements on bodies. In addition to a wide variety of mechanical devices that have been used, in some cases for many years, there have also been techniques developed in which some kind of light pattern is directed onto the body and the shape or position of that light pattern sensed and, as a result, certain measurements related to the body sensed. Such prior techniques have proved adequate when making a limited number of localized measurements on a body but have not been able, at least without resorting to extremely complex arrangements, to make sufficient measurements that for example the shape of a large part or even all of a human body can be derived. Another technique that has been employed is to place a light source on one side of a body and an array of light detectors on the other side of the body. The boundary of the shadow cast by the body is then determined by the array of detectors. A technique of this kind is simpler than the optical techniques referred to above, but has the disadvantage of providing only a measurement of that part of the body that protrudes furthest. This makes interpretation and processing of data relatively complicated and also means that re-entrant surfaces on the body are not detected at all.

SUMMARY OF THE INVENTION

It is an object of the present invention to provide a method and apparatus for making measurements on a body which while not being unduly complex is accurate and which provides measurement data in a form which can readily be interpreted and processed.

The present invention provides a method of making measurements on a body including the steps of placing the body in a space which is divided along a plane into adjacent regions of contrasting illumination with the dividing plane intersecting the body, and sensing the position on the dividing plane of at least a part of the exterior surface of the body with a sensor sensitive to the illumination at a plurality of relative positions of the body and the dividing plane.

With such an arrangement measurements can be made all the way around the body.

The sensing at a plurality of relative positions of the body and the dividing plane may be achieved by generating a plurality of dividing planes each at a different relative position to the body, but is preferably achieved by movement of the body relative to the dividing plane. Such movement may be translational movement but preferably the body is rotated about an axis relative to the dividing plane. Preferably, the axis about which the body is rotated lies in the dividing plane. In this case the distance of the exterior surface of the body from the axis of rotation (i.e. the radius of the body) can be directly sensed and this facilitates derivation of the shape of the body from the measurements.

The adjacent regions of contrasting illumination may be illuminated with radiation of different wave-lengths, which need not be in the visible spectrum, but it is preferred for simplicity to have contrasting intensity of the same radiation, for example white light, that is to have a bright region and a dark region. In such a case the dividing plane will define the boundary between the bright region and the dark region. An alternative arrangement within the scope of the invention would be to define the dividing plane by a wide but very thin beam of light on either side of which were relatively dark regions; in that case the beam itself would define the "plane".

The space in which the body is placed is preferably divided into just two regions. The division of the space can be accomplished by one or more light sources located on the dividing plane and providing contrasting illumination to each side of the plane. Light sources may be provided on each of the opposite sides of the body as in the embodiment described below with reference to the drawings.

The sensor may be a camera spaced from and directed towards the body with that part of the exterior surface of the body whose position is to be sensed within the field of view of the camera.

The plane containing the axis of rotation of the body and the camera preferably makes an angle of between 30° and 60° with the dividing plane and more preferably makes an angle of about 45° with the dividing plane. In such a case, the camera is sufficiently spaced from the dividing plane to provide an indication of the distance of the exterior surface of the body from the axis of rotation while at the same time the viewing direction of the camera is sufficiently close to alignment with the dividing plane for its view of the intersection of the dividing plane with the body not to be obstructed by a protuberance on the body, apart from exceptional cases. An alternative arrangement would be to place the camera so that the plane containing it and the axis of rotation of the body is perpendicular to the dividing plane. This arrangement provides a direct indication of the distance of the exterior surface of the body from the axis of rotation but does not readily allow for any protuberances or recesses on the body. To enable the arrangement to cope much better with such protuberances or recesses a second camera, placed so that the plane containing it and the axis of rotation of the body is inclined to the dividing plane, may be provided in addition to the camera in the plane perpendicular to the dividing plane.

A pair of sensors may be provided on the same side of the dividing plane but to opposite sides of the body, one sensor of the pair sensing the intersection of one side of the body with the dividing plane and the other sensor of the pair sensing the intersection of the other side of the body with the dividing plane. With such an arrangement a diametric measurement can be made on the body so that movement of the body such as is liable to occur during rotation of a living human body, has little effect on the accuracy of the measurement.

A variety of techniques may be employed for counteracting the effects of body sway on the measurements. One technique would be to provide further sensors to measure movement of the body in orthogonal directions. Such sensors may for example comprise ultrasonic devices or cameras.

A plurality of sensors or pairs of sensors may be provided.

A signal from the sensor may be processed to provide a display on a display unit showing the shape of the interface of the dividing plane with at least a part of the exterior surface of the body. In a case where the sensor is a video camera the display unit may be a video display unit (VDU). In addition to or instead of the display on the display unit signals from the sensor may be passed to an electronic processing unit which may have an output connected to a memory.

In general it is convenient for the body to be rotated while the dividing plane and sensor(s) remain stationary, but if desired, the dividing plane and sensor(s) may be rotated while the body remains stationary. The latter arrangement has the disadvantage that the apparatus as a whole has to be bulkier and is less portable but has the advantage that the speed of rotation is not restricted as it is when a human body is rotated so that measurements around the whole body can be made more quickly.

The invention also provides an apparatus for making measurements on a body placed in a space, the apparatus including a source of illumination arranged to divide the space along a plane into adjacent regions of contrasting illumination and a sensor for sensing the position on the dividing plane of at least a part of the exterior surface of a body placed in the space, the arrangement being such that the sensing of the position on the dividing plane of at least a part of the exterior surface of the body can be carried out at a plurality of relative positions of the body and the dividing plane.

Other preferable features of the apparatus of the invention will be apparent from the preferred features of the method of the invention recited above.

BRIEF DESCRIPTION OF THE DRAWINGS

By way of example an embodiment of the invention will now be described with reference to the accompanying drawings, of which.

DETAILED DESCRIPTION OF THE PREFERRED EMBODIMENTS

Figure 1:
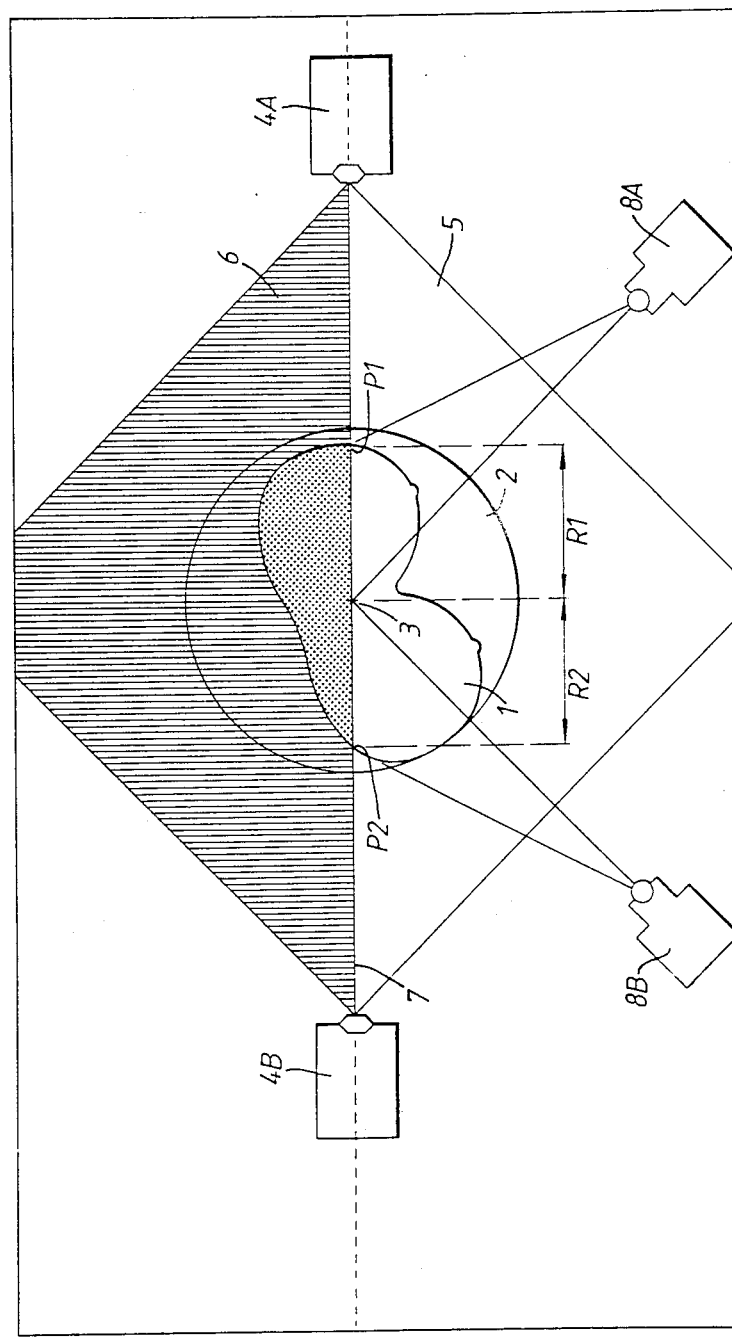
FIG. 1 is a plan view of an apparatus for making a measurement on a body with the body shown in section.

FIG. 1 shows a body 1 mounted approximately centrally on a turntable 2 rotatable about an axis 3. A pair of slide projectors 4A and 4B are provided on opposite sides of the body 1 and each operate with a slide which divides the illumination from the projector into a brightly illuminated area 5 and a dark area 6. The boundary between the bright area 5 and the dark area 6 defines a dividing plane 7 which passes through the axis 3. Video cameras 8A and 8B view the body with the camera 8A set up to view the area immediately to the right (as seen in the drawing) of the axis 3 and the camera 8B set up to view the area immediately to the left (as seen in the drawing) of the axis 3.

As can be most readily understood by referring to FIG. 1, the camera 8A sees a bright region extending from the axis 3 to the right as far as the point P1 at which the exterior surface of the body 1 cuts the dividing plane 7 and further to the right sees a dark region. The distance of the point P1 from the axis 3 is the radius R1 of the body at that position. Similarly camera 8B sees a bright region extending from the axis 3 to the left as far as the point P2 at which the exterior surface of the body 1 again cuts the dividing plane 7 and further to the left sees a dark region. The distance of the point P2 from the axis 3 is the radius R2 of the body at that position. The sum of the radii R1 and R2 gives the diameter or width of the body on the dividing plane.

Figure 2:
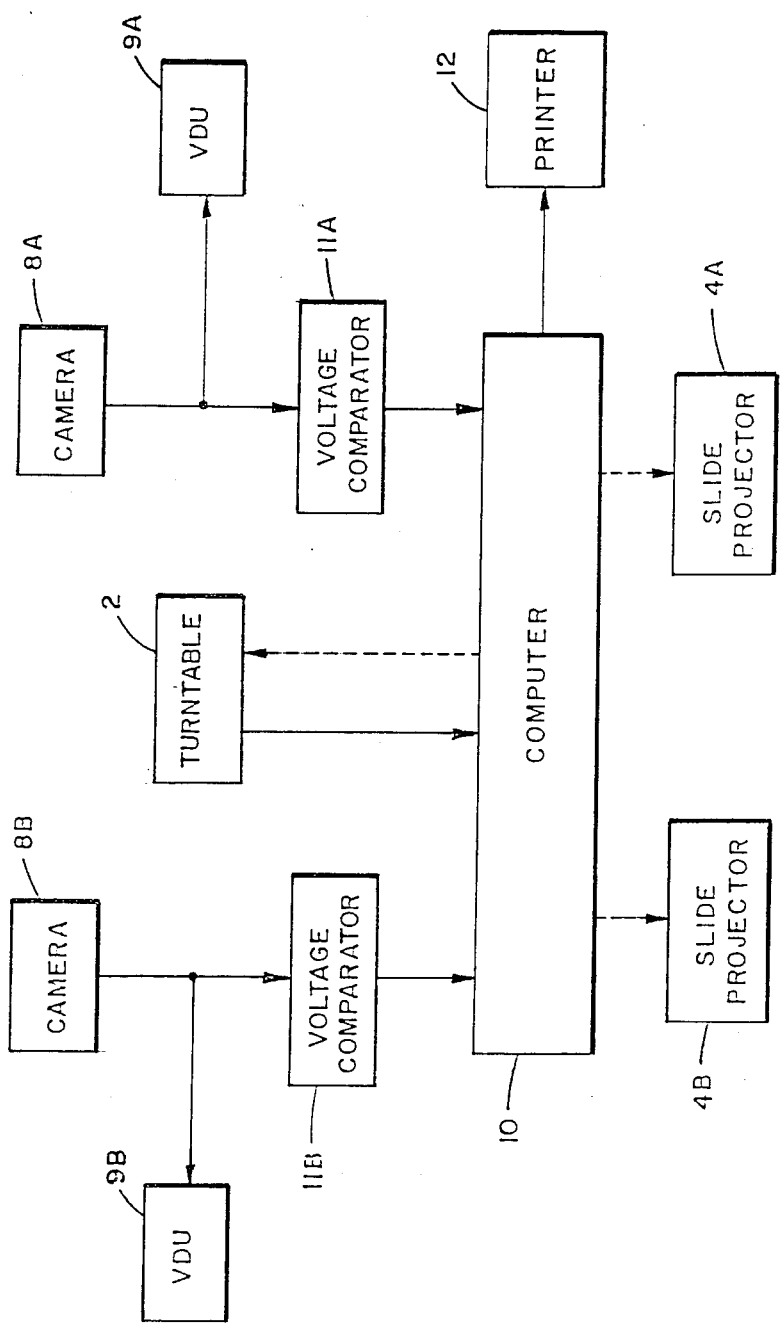
FIG. 2 is a schematic block diagram showing how different parts of the apparatus are interconnected.

Referring now to FIG. 2, the outputs of the cameras 8A, 8B are connected to respective VDU's 9A, 9B and to a common computer 10. The signal from each camera is a varying analogue signal instantaneously representing the light level of a particluar part of the scene being viewed. These signals are fed to the computer 10 via voltage comparators 11A and 11B which are preset to detect a voltage above that which corresponds to a particular light level; the comparators 11A and 11B have a two stage output: one state corresponds to a bright area and is the signal the camera receives from any part of the body situated in the bright area 5 and the other state corresponds to a dark area and is the signal the camera receives both from any part of the body situated in the dark area 6 and also from any part of the area outside the body.

The computer 10 also receives an input from the turntable 2 indicating the rotational position of the turntable and may have outputs controlling the projectors 4A, 4B and/or the rotation of the turntable 2, such outputs being shown by dotted lines in FIG. 2.

FIG. 2 also shows an output of the computer 10 connected to a printer 12.

The camera 8A, for example, provides a signal to the VDU 9A and the computer 10 which is a conventional video signal and thus consists of a series of line scans across the field of view of the camera. The start of a line scan coincides with the axis 3 and in each line scan the camera detects brightness until it reaches the intersection of the body exterior with the dividing plane 7 (point P1) and thereafter the camera detects darkness; thus the length of the illuminated portion of the line scan provides a measure of the radius (R1) of the body at that point; the length of the next line scan provides a measure of the radius of the body just below the previous scan and so on.

If the camera 8A is conventional then the relationship between the length of the illuminated portion of the line scan and the radius of the body will be approximately, but not exactly, linear. However this non-linearity can be compensated for either in the camera or in the computer.

The second camera 8B can operate in exactly the same way as the camera 8A although of course in this case the camera, if it operates in the same way as the camera 8A will finish a line scan at the axis 3 rather than starting the line scan there. It will be clear, however, to those skilled in the art that this difference may readily be allowed for by the computer 10.

If the body 1 is a human body, then it will be appreciated that the height of the body when standing on the turntable 2 will be several times even its largest diameter. In order for the measurements of the body to be accurate it is desirable that at its widest point the body should substantially fill the field of view of the cameras. If, for example, the maximum width of the body were 80 cm then the width of the field of view of the camera 8A would have to be of the order of 30 cm which with a conventional camera would provide a field of view whose height was about 21 cm. Clearly therefore, in order to make measurements the whole way up a human body it would be necessary to provide additional cameras above or below the cameras 8A, 8B or to move the cameras up or down between series of measurements.

In order to measure all around the body 1, the turntable 2 may be rotated by a small increment such as 5° or 10° between each set of measurements. It will be noted that because cameras 8A and 8B make measurements on opposite sides of the body at any one time, measurements all the way around the body can be obtained by rotating the body through only 180°. Nevertheless, it may still be preferable to rotate the body through an entire revolution thereby obtaining duplication of measurements since it is then possible for the computer 10 to take account of false readings due either to movement of the body or to sharply angled protuberances or recesses being undetected by one of the cameras.

The computer 10 may provide an output to the printer 12 to give tabulated data or a perspective view or a particular side or sectional view of all or part of the body or some other information. The computer 10 might also, or instead, be connected to control the operation of some other sort of machine; in one example of the invention that other machine might create a pattern from which clothing for the measured body was to be produced. It will be appreciated that these are merely examples of outputs that might be produced and there are many further possibilities.

While certain specific embodiments of the invention have been described it should be understood that there may be many variations to these embodiments. For example instead of rotating the body 1 in incremental steps it might be possible to rotate the body continously. While a video camera is a convenient form of sensor some other kind of sensor sensitive to the radiation projected by the projectors 4A and 4B might be used. The number of projectors and also the number of cameras may be reduced to just one or increased. For example further projectors could be located on the dividing plane above or below the projectors 4A and 4B. Although it is advantageous to provide the computer 10, this device may be replaced by an electronic memory which merely records the data and does not process it; such an alternative arrangement might be particularly suitable if the apparatus were being used in the field, in which case the data in the memory could be processed upon return to a central work station.

In the embodiment shown in the drawing the body is rotated relative to the dividing plane. An alternative arrangement would be to move the body translationally relative to the dividing plane and to make measurements at a multiplicity of incremental steps of movement across the body. Such an alternative arrangement can be understood with reference to the apparatus of FIG. 1; if in that apparatus, the turntable 2 were replaced by a table mounted for movement perpendicular to the dividing plane 7 the body 1 could be moved in small steps translationally across the dividing plane and at each position the distances $R_1$, $R_2$ measured by the cameras 8A, 8B; in this alternative arrangement it would also be desirable to have cameras positioned on the opposite side of the dividing plane 7 to the cameras 8A, 8B. The translational measurement may be horizontal, vertical or in any other direction. As an alternative to moving the body 1, the projectors and cameras may be moved or the dividing plane alone may be moved either by moving the projectors or by including an optical arrangement for generating the dividing plane in a multiplicity of planes across the body (an optical technique may also be used for generating dividing planes that are rotationally spaced from one another, as required in the case where the body is rotated relative to the dividing plane).

It is important to distinguish the method of the present invention from that using a silhouette technique with a light source on one side of the body and an array of detectors on the other side. The disadvantages of such a technique have already been referred to. It should also be understood however that the method of the present invention may be used in conjunction with a silhouette technique and measurements obtained from both techniques used together.

The invention thus provides a technique which is capable of making measurements all around a human body and of using those measurements to provide a complete indication of the shape and size of the body. The invention may for example be used in the textile industry either by measuring a large number of people and generating from the measurements statistical data from which appropriately sized clothing may be made, or by measuring a single individual and, either as a separate manual step or even as an automatic process, creating clothing tailored to the specific shape of that individual. The invention may also be used in the medical industry to enable an artificial part of a body to be matched in shape exactly to an original part which for medical or other reasons has to be removed. For example, the invention may be employed to create an artificial breast for a woman who has a mastectomy.

We claim:

1. A method of making measurements on a body including the steps of:
    placing the body in a space which is divided along a plane into adjacent regions of contrasting illumination with the dividing plane intersecting the body;
    rotating the body relative to the dividing plane about an axis which lies in the dividing plane; and
    sensing the position on the dividing plane of at least a part of the exterior surface of the body with sensor means sensitive to the illumination at a plurality of relative rotational positions of the body and the dividing plane.

2. A method as claimed in claim 1 in which the space is divided into adjacent regions of contrasting illumination by one or more light sources located on the dividing plane.

3. A method as claimed in claim 1 in which the sensor means is a camera.

4. A method as claimed in claim 5 in which the optical axis of the camera makes an angle of between 30° and 60° with the dividing plane.

5. A method as claimed in claim 1 in which a plurality of sensor means are provided.

6. An apparatus for making measurements on a body placed in a space, the apparatus including:
    a source of illumination arranged to divide the space along a plane into adjacent regions of contrasting illumination;
    sensor means for sensing the position on the dividing plane of at least a part of the exterior surface of a body placed in the space; and
    rotary mounting means for mounting the body for rotation relative to the dividing plane about an axis which lies in the dividing plane.

7. An apparatus as claimed in claim 6 in which the source of illumination is located on the dividing plane.

8. An apparatus as claimed in any of claim 6 in which the sensor means is a camera.

9. An apparatus as claimed in claim 8 in which the optical axis of the camera makes an angle of between 30° and 60° with the dividing plane.

10. An apparatus as claimed in any of claim 6 in which a plurality of sensor means are provided.

* * * * *